(12) United States Patent
Lau et al.

(10) Patent No.: US 7,893,017 B2
(45) Date of Patent: Feb. 22, 2011

(54) PROTRACTED GLP-1 COMPOUNDS

(75) Inventors: Jesper Lau, Farum (DK); Thomas Kruse Hansen, Herlev (DK)

(73) Assignee: Novo Nordisk A/S, Bagsvaerd (DK)

( * ) Notice: Subject to any disclaimer, the term of this patent is extended or adjusted under 35 U.S.C. 154(b) by 18 days.

(21) Appl. No.: 11/664,788

(22) PCT Filed: Oct. 7, 2005

(86) PCT No.: PCT/EP2005/055101

§ 371 (c)(1),
(2), (4) Date: Nov. 19, 2007

(87) PCT Pub. No.: WO2006/037810

PCT Pub. Date: Apr. 13, 2006

(65) Prior Publication Data

US 2008/0182785 A1       Jul. 31, 2008

Related U.S. Application Data

(60) Provisional application No. 60/621,022, filed on Oct. 21, 2004, provisional application No. 60/664,498, filed on Mar. 23, 2005.

(30) Foreign Application Priority Data

Oct. 7, 2004   (DK) .............................. 2004 01535
Mar. 18, 2005  (EP) ................................ 05102168

(51) Int. Cl.
   *A61K 38/26*   (2006.01)
(52) U.S. Cl. ........................................ 514/1.1; 530/308
(58) Field of Classification Search ........................ None
   See application file for complete search history.

(56) References Cited

U.S. PATENT DOCUMENTS

| 5,424,286 A | 6/1995 | Eng |
| 6,451,970 B1 * | 9/2002 | Schaffer et al. ............. 530/303 |
| 2001/0047084 A1 | 11/2001 | Knudsen et al. |
| 2004/0146985 A1 | 7/2004 | Sun et al. |
| 2008/0249007 A1 | 10/2008 | Lau et al. |

FOREIGN PATENT DOCUMENTS

| EP | 1386930 | 2/2004 |
| WO | 96/29342 | 9/1996 |
| WO | 98/08871 | 3/1998 |
| WO | WO 98/08871 | 3/1998 |
| WO | 99/43341 | 9/1999 |
| WO | 99/43706 | 9/1999 |
| WO | 99/43708 | 9/1999 |
| WO | WO 99/43708 | 9/1999 |
| WO | 00/34331 | 6/2000 |
| WO | WO 00/55119 | 9/2000 |
| WO | 00/69911 | 11/2000 |
| WO | WO 00/66629 | 11/2000 |
| WO | WO 01/04156 | 1/2001 |
| WO | 01/98331 | 12/2001 |
| WO | 02/46227 | 6/2002 |
| WO | 03/002136 | 1/2003 |
| WO | WO 03/011892 | 2/2003 |
| WO | 2004/005342 | 1/2004 |
| WO | WO 2004/089985 | 10/2004 |
| WO | WO 2005/027978 | 3/2005 |
| WO | WO 2006/037810 | 4/2006 |
| WO | WO 2006/051103 | 5/2006 |
| WO | WO 2006/097535 | 9/2006 |
| WO | WO 2006/097537 | 9/2006 |
| WO | WO 2006/097538 | 9/2006 |

OTHER PUBLICATIONS

Knudsen, L.B., Potent Derivatives of Glucagon-Like Peptide-1 With Pharmacokinetic Properties Suitable for Once Daily Administration, Journal of Medicinal Chemistry, vol. 43(9), 1664-9 (2000).
Knudsen, L.B., Glucagon-Like Peptide-1: The Basis of a New Class of Treatment for Type-2 Diabetes, Journal of Medicinal Chemistry, vol. 47(17), pp. 4128-4134 (2004).
Adelhorst, K. et al., Structure-Activity Studies of Glucagon-Like Peptide-1, Journal of Biological Chemistry, vol. 269(9), pp. 6275-6278 (1994).
Holz, G.G. et al., Glucagon-Like Peptide-1 Synthetic Analogs; New Therapeutic Agents for Us in the Treatment of Diabetes Mellitus, Current Medicinal Chemistry, vol. 10(22), pp. 2471-2483 (2003).
Deacon, C. F. et al, Dipeptidyl peptidase IV resistant analogues of glucagon-like peptide-1 which have extended metabolic stability and improved biological activity, Diabetologia, 1998, 271-278, vol. 41.
Green, Brian D. et al, Degradation receptor binding insulin secreting and antihype glycaemic actions of palmitate-derivatised native and Ala-substituted GLP-1 analogues, Biol. Chem., 2004, 169-177, vol. 385—No. 2.
Green, Brian D. et al, N-terminal His-modification of glucagon-like peptide-1 (7-36) amide generates dipeptidyl peptidase IV-stable analogues with potent antihyperglycaemic activity, Journal of Endocrinology, 2004, 379-288, vol. 180—No. 3, Society for Endocrinology, printed in Great Britain.
Gallwitz, B. et al, GLP-1-analogues resistant to degradation by dipeptidyl-peptidase IV in vitro, Regulatory Peptides, 2000, 103-111, vol. 86—No. 1-3, Elsevier Science.
Non-Final Office Action mailed Nov. 4, 2009 in U.S. Appl. No. 11/664,785 filed Apr. 5, 2007 by Lau et al.
Non-Final Office Action mailed Jul. 1, 2010 in U.S. Appl. No. 11/664,785 filed Apr. 5, 2007 by Lau et al.

* cited by examiner

*Primary Examiner* — Robert Landsman
*Assistant Examiner* — Gyan Chandra
(74) *Attorney, Agent, or Firm* — Richard W. Bork

(57) ABSTRACT

Novel protracted GLP-1 compounds and therapeutic uses thereof.

8 Claims, No Drawings

SEQUENCE LISTING

<160> NUMBER OF SEQ ID NOS: 6

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 32
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (32)..(32)
<223> OTHER INFORMATION: Lys is substituted

<400> SEQUENCE: 2

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Lys
            20                  25                  30

<210> SEQ ID NO 3
<211> LENGTH: 32
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (32)..(32)
<223> OTHER INFORMATION: Lys is substituted

<400> SEQUENCE: 3

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Lys
            20                  25                  30

<210> SEQ ID NO 4
<211> LENGTH: 32
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is alfahydroxydesamino histidine
<220> FEATURE:
<221> NAME/KEY: MISC_FEATURE
<222> LOCATION: (32)..(32)
<223> OTHER INFORMATION: Lys is substituted

<400> SEQUENCE: 4

-continued

```
Xaa Gly Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Lys
            20                  25                  30

<210> SEQ ID NO 5
<211> LENGTH: 32
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (32)..(32)
<223> OTHER INFORMATION: Lys is substituted

<400> SEQUENCE: 5

His Gly Glu Gly Thr Phe Thr Ser Asp Val Ser Arg Tyr Leu Glu Glu
1               5                   10                  15

Glu Ala Ala Arg Glu Phe Ile Glu Trp Leu Val Arg Gly Arg Gly Lys
            20                  25                  30

<210> SEQ ID NO 6
<211> LENGTH: 32
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (32)..(32)
<223> OTHER INFORMATION: Lys is substituted

<400> SEQUENCE: 6

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Lys
            20                  25                  30
```

PROTRACTED GLP-1 COMPOUNDS

CROSS-REFERENCE TO RELATED APPLICATIONS

This application is a 35 U.S.C. §371 national stage application of International Patent Application PCT/EP2005/055101 (published as WO 2006/037810), filed Oct. 7, 2005, which claimed priority of Danish Patent Application PA 2004 01535, filed Oct. 7, 2004; and European Patent Application 05102168.1, filed Mar. 18, 2005; this application further claims priority under 35 U.S.C. §119 of U.S. Provisional Application 60/621,022, filed Oct. 21,2004; and U.S. Provisional Application 60/664,498, filed Mar. 23, 2005.

FIELD OF THE INVENTION

The present invention relates to the field of therapeutic peptides, i.e. to new protracted GLP-1 compounds.

BACKGROUND OF THE INVENTION

A range of different approaches have been used for modifying the structure of glucagon-like peptide 1 (GLP-1) compounds in order to provide a longer duration of action in vivo. WO 96/29342 discloses peptide hormone derivatives wherein the parent peptide hormone has been modified by introducing a lipophilic substituent in the C-terminal amino acid residue or in the N-terminal amino acid residue.

WO 98/08871 discloses GLP-1 derivatives wherein at least one amino acid residue of the parent peptide has a lipophilic substituent attached.

WO 99/43708 discloses GLP-1 (7-35) and GLP-1 (7-36) derivatives which have a lipophilic substituent attached to the C-terminal amino acid residue.

WO 00/34331 discloses acylated GLP-1 analogs.

WO 00/69911 discloses activated insulinotropic peptides to be injected into patients where they are supposed to react with blood components to form conjugates and thereby allegedly providing longer duration of action in vivo.

WO 02/46227 discloses GLP-1 and exendin-4 analogs fused to human serum albumin in order to extend in vivo half-life.

Many diabetes patients particularly in the type 2 diabetes segment are subject to so-called "needle-phobia", i.e. a substantial fear of injecting themselves. In the type 2 diabetes segment most patients are treated with oral hypoglycemic agents, and since GLP-1 compounds are expected to be the first injectable product these patients will be administered, the fear of injections may become a serious obstacle for the widespread use of the clinically very promising GLP-1 compounds. Thus, there is a need to develop new GLP-1 compounds which can be administered less than once daily, e.g. once every second or third day preferably once weekly, while retaining an acceptable clinical profile.

SUMMARY OF THE INVENTION

The present invention provides DPP-IV stabilised GLP-1 analogs acylated with a diacid. The present invention also provides an acylated GLP-1 analog where said GLP-1 analog is stabilised against DPP-IV by modification of at least one amino acid residue in positions 7 and 8 relative to the sequence GLP-1 (7-37) (SEQ ID No 1), and where said acylation is a diacid attached directly to the C-terminal amino acid residue of said GLP-1 analog. The present invention also provides a DPP-IV stabilised GLP-1 analog, wherein said GLP-1 analog comprises a modification at the N-terminal, such as a modification of the natural $His^7$ or $Ala^8$.

The present invention also provides a DPP-IV stabilised GLP-1 analog acylated with a diacid, wherein said diacid is attached to the epsilon amino group of a lysine residue of said GLP-1 analog.

The present invention also provides a DPP-IV stabilised GLP-1 analog acylated with a diacid, wherein acylation is on $Lys^{38}$ of said GLP-1 analog.

The present invention also provides a method for increasing the time of action in a patient of a GLP-1 analog to more than about 40 hours, characterised in modifying at least one of the amino acid residues in positions 7 and 8 of a GLP-1 (7-37) peptide or an analog thereof, and directly acylating the C-terminal amino acid residue of the GLP-1 analog with a diacid.

The present invention also provides pharmaceutical compositions comprising a compound according to the present invention and the use of compounds according to the present invention for preparing medicaments for treating disease.

DEFINITIONS

In the present specification, the following terms have the indicated meaning:

The term "polypeptide" and "peptide" as used herein means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g. hydroxyproline, γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), β-alanine, 3-aminomethyl benzoic acid, anthranilic acid.

The term "analog" as used herein referring to a polypeptide means a modified peptide wherein one or more amino acid residues of said polypeptide have been substituted by other amino acid residues and/or wherein one or more amino acid residues have been deleted from said polypeptide and/or wherein one or more amino acid residues have been deleted from said polypeptide and or wherein one or more amino acid residues have been added to the peptide. Such addition or deletion of amino acid residues can take place at the N-terminal of the peptide and/or at the C-terminal of the peptide.

The term "derivative" as used herein in relation to a peptide means a chemically modified peptide or an analogue thereof, wherein at least one substituent is not present in the unmodified peptide or an analogue thereof, i.e. a peptide which has been covalently modified. Typical modifications are amides, carbohydrates, alkyl groups, acyl groups, esters and the like.

An example of a derivative of GLP-1 (7-37) is Arg$^{34}$, Lys$^{26}$ (N$^\epsilon$-($\gamma$-Glu(N$^\alpha$-hexadecanoyl)))-GLP-1(7-37).

The term "GLP-1" as used herein means GLP-1 (7-37) (SEQ ID No:1), an analog of GLP-1 (7-37), a GLP-1 (7-37) derivative, a derivative of a GLP-1 (7-37) analog or fusion proteins comprising GLP-1 (7-37) or a GLP-1 (7-37) analog or derivative. In one embodiment GLP-1 is an insulinotropic agent.

The term "insulinotropic agent" as used herein means a compound which is an agonist of the human GLP-1 receptor, i.e. a compound which stimulates the formation of cAMP in a suitable medium containing the human GLP-1 receptor. The potency of an insulinotropic agent is determined by calculating the EC$_{50}$ value from the dose-response curve as described below.

Purified plasma membranes from a stable transfected cell line, BHK467-12A (tk-ts13), expressing the human GLP-1 receptor were stimulated with GLP-1 and peptide analogues, and the potency of cAMP production was measured using the AlphaScreen™ cAMP Assay Kit from Perkin Elmer Life Sciences.

A stable transfected cell line was prepared and a high expressing clone was selected for screening. The cells were grown at 5% CO$_2$ in DMEM, 5% FCS, 1% Pen/Strep and 0.5 mg/ml G418.

Cells at approximate 80% confluence were washed twice with PBS and harvested with Versene, centrifuged 5 min at 1000 rpm and the supernatant removed. The additional steps were all made on ice. The cell pellet was homogenized by the Ultrathurax for 20-30 sec. in 10 ml of Buffer 1 (20 mM Na-HEPES, 10 mM EDTA, pH=7.4), centrifuged 15 min at 20.000 rpm and the pellet resuspended in 10 ml of Buffer 2 (20 mM Na-HEPES, 0.1 mM EDTA, pH=7.4). The suspension was homogenized for 20-30 sec and centrifuged 15 min at 20.000 rpm. Suspension in Buffer 2, homogenization and centrifugation was repeated once and the membranes were resuspended in Buffer 2 and ready for further analysis or stored at −80° C.

The functional receptor assay was carried out by measuring the peptide induced cAMP production by The AlphaScreen Technology. The basic principle of The AlphaScreen Technology is a competition between endogenous cAMP and exogenously added biotin-cAMP. The capture of cAMP is achieved by using a specific antibody conjugated to acceptor beads. Formed cAMP was counted and measured at a AlphaFusion Microplate Analyzer. The EC$_{50}$ values were calculated using the Graph-Pad Prisme software.

The term "DPP-IV protected" as used herein in reference to a polypeptide means a polypeptide which has been chemically modified in order to render said compound more resistant to the plasma peptidase dipeptidyl aminopeptidase-4 (DPP-IV) than the chemically unmodified peptide. The DPP-IV enzyme in plasma is known to be involved in the degradation of several peptide hormones, e.g. GLP-1, GLP-2, etc.

Resistance of a peptide to degradation by dipeptidyl aminopeptidase IV may be determined by the following degradation assay:

Aliquots of the peptide are incubated at 37° C. with an aliquot of purified dipeptidyl aminopeptidase IV for 4-22 hours in an appropriate buffer at pH 7-8 (buffer not being albumin). Enzymatic reactions are terminated by the addition of trifluoroacetic acid, and the peptide degradation products are separated and quantified using HPLC or LC-MS analysis. One method for performing this analysis is: The mixtures are applied onto a Zorbax 300SB-C18 (30 nm pores, 5 μm particles) 150×2.1 mm column and eluted at a flow rate of 0.5 ml/min with a linear gradient of acetonitrile in 0.1% trifluoroacetic acid (0%-100% acetonitrile over 30 min). Peptides and their degradation products may be monitored by their absorbance at 214 nm (peptide bonds) or 280 nm (aromatic amino acids), and are quantified by integration of their peak areas. The degradation pattern can be determined by using LC-MS where MS spectra of the separated peak can be determined. Percentage intact/degraded peptide at a given time is used for estimation of the peptide's DPPIV stability.

In one embodiment, a peptide is defined as DPP IV stabilised when it is 10 times more stable than the natural peptide based on percentage intact compound at a given time. Thus, a DPPIV stabilised GLP-1 compound is at least 10 times more stable than GLP-1 (7-37).

DETAILED DESCRIPTION OF THE INVENTION

In one aspect the present invention relates to a DPP-IV stabilised GLP-1 analog acylated with a diacid.

In another aspect the present invention relates to an acylated GLP-1 analog where said GLP-1 analog is stabilised against DPP-IV by modification of at least one amino acid residue in positions 7 and 8 relative to the sequence GLP-1 (7-37) (SEQ ID No 1), and where said acylation is a diacid attached directly to the C-terminal amino acid residue of said GLP-1 analog.

In one embodiment of the invention said diacid is attached to the epsilon amino group of a lysine residue of said GLP-1 analog.

In another embodiment of the invention said GLP-1 analog has an extended C-terminal, eg. the analog comprises an amino acid residue in position 38 relative to the sequence GLP-1 (7-37) (SEQ ID No. 1). Such analogs may even comprise amino acid residues in position 39, 40, 41 etc.

In another embodiment of the invention said diacid is attached to a Lys$^{38}$ of said GLP-1 analog.

In another embodiment of the invention said diacid is attached to a Lys$^{39}$ of said GLP-1 analog.

In another embodiment of the invention said diacid is attached to a Lys$^{40}$ of said GLP-1 analog.

In another embodiment of the invention said diacid is attached to a Lys$^{41}$ of said GLP-1 analog.

In another embodiment of the invention said diacid is attached to a Lys$^{37}$ of said GLP-1 analog.

In another embodiment of the invention said GLP-1 analog comprises a modification at the N-terminal, such as a modification of the natural His$^7$ or Ala$^8$.

In yet another embodiment of the invention said GLP-1 analog is a position 7 analog wherein the natural His$^7$ has been substituted by imidazopropionyl$^7$, α-hydroxy-histidine$^7$ or N-methyl-histidine.

In yet another embodiment of the invention said GLP-1 analog is a position 7 analog wherein the natural His⁷ has been substituted by D-histidine⁷, desamino-histidine⁷, 2-amino-histidine⁷, β-hydroxy-histidine⁷, homohistidine⁷, N$^\alpha$-acetyl-histidine⁷, α-fluoromethyl-histidine⁷, α-methyl-histidine⁷, 3-pyridylalanine⁷, 2-pyridylalanine⁷ or 4-pyridylalanine⁷.

In yet another embodiment of the invention said GLP-1 analog is a position 8 analog wherein the natural Ala⁸ has been substituted by Aib⁸, Gly⁸, Val⁸, Ile⁸, Leu⁸, Ser⁸ or Thr⁸.

In yet another embodiment of the invention said GLP-1 analog comprises a substitution of the L-alanine in position 8 of GLP-1 (7-37) sequence for (1-aminocyclopropyl)carboxylic acid, (1-aminocyclobutyl)carboxylic acid, (1-aminocyclopentyl)carboxylic acid, (1-aminocyclohexyl)carboxylic acid, (1-aminocycloheptyl)carboxylic acid, or (1-aminocyclooctyl)carboxylic acid.

In yet another embodiment of the invention said GLP-1 analog comprises a substitution of the natural Gly in position 22 for a Glu residue.

In yet another embodiment of the invention said GLP-1 analog comprises a substitution of the natural Val in position 16 for a Leu residue.

In yet another embodiment of the invention said GLP-1 analog comprises a substitution of the natural Ala in position 30 for a Glu residue.

In yet another embodiment of the invention the diacid is a dicarboxylic acid.

In yet another embodiment of the invention the acylation group is a straight-chain or branched alkane α,ω-dicarboxylic acid.

In yet another embodiment of the invention the acylation group has the structure HOOC—$(CH_2)_n$CO—, wherein n is 12 to 20.

In yet another embodiment of the invention the acylation group has a structure selected from HOOC—$(CH_2)_{14}$CO—, HOOC—$(CH_2)_{15}$CO—, HOOC—$(CH_2)_{16}$CO—, HOOC—$(CH_2)_{17}$CO—, and HOOC—$(CH_2)_{18}$CO—.

In yet another embodiment of the invention the acylation group has the structure HOOC—$(CH_2)_{16}$CO—.

In yet another embodiment of the invention said GLP-1 analog comprises no more than fifteen amino acid residues which have been exchanged, added or deleted as compared to GLP-1 (7-37) (SEQ ID No. 1), or no more than ten amino acid residues which have been exchanged, added or deleted as compared to GLP-1 (7-37) (SEQ ID No. 1).

In yet another embodiment of the invention said GLP-1 analog comprises no more than six amino acid residues which have been exchanged, added or deleted as compared to GLP-1 (7-37) (SEQ ID No. 1).

In yet another embodiment of the invention said GLP-1 analog comprises no more than 6 amino acid residues which are not encoded by the genetic code.

In yet another embodiment of the invention said GLP-1 analog comprises no more than 5 amino acid residues which are not encoded by the genetic code.

In yet another embodiment of the invention said GLP-1 analog comprises no more than 4 amino acid residues which are not encoded by the genetic code.

In yet another embodiment of the invention said GLP-1 analog comprises no more than 3 amino acid residues which are not encoded by the genetic code.

In yet another embodiment of the invention said GLP-1 analog comprises no more than 2 amino acid residues which are not encoded by the genetic code.

In yet another embodiment of the invention said GLP-1 analog comprises no more than one amino acid residue which is not encoded by the genetic code.

In yet another embodiment of the invention said GLP-1 analog comprises only one lysine residue.

In yet another embodiment of the invention, the DPP-IV stabilised GLP-1 analog which is acylated with a diacid directly on the C-terminal amino acid residue is [Aib8,Arg26, 34]GLP-1 (7-37)Lys{17-carboxyheptadecanoyl}-OH

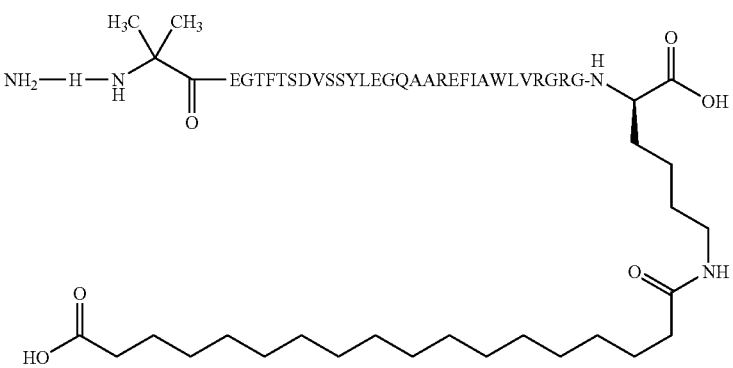

or [Gly8,Arg26,34,36]GLP-1 (7-37) Lys(17-Carboxyhepta-decanoylamino)-OH
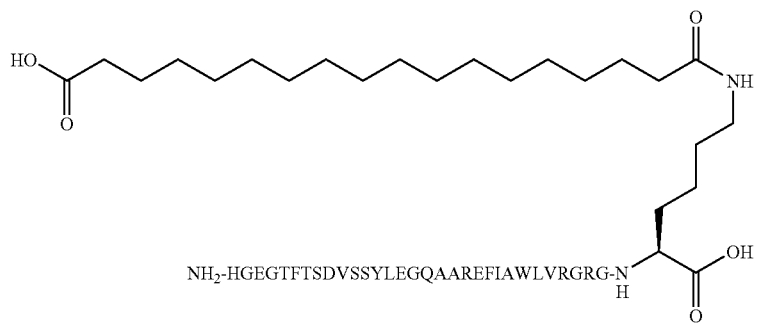
or [AlfahydroxydesaminoHis7, Gly8, Arg26,34]GLP-1 (7-37)Lys(17-carboxyheptadecanoyl)-OH
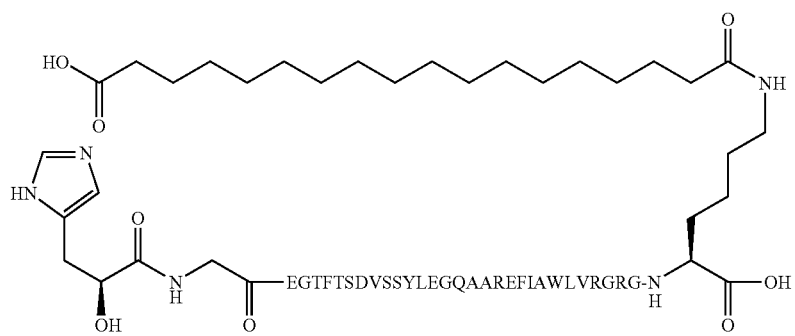
or [Gly8, Glu22,23,30, Arg 18,26,34]GLP1 (7-37) Lys(17-carboxyheptadecanoyl)-NH2
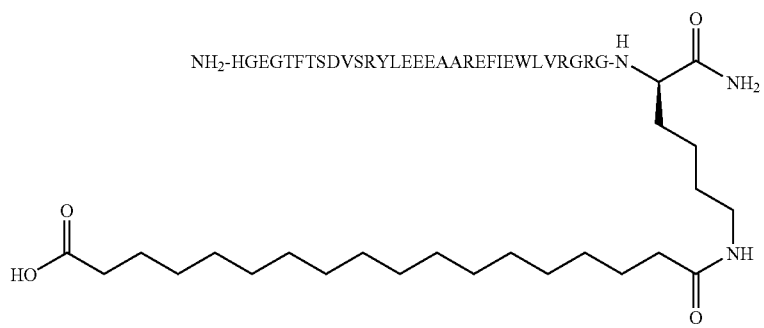

or [Gly8,Arg26,34]GLP-1 (7-37)Lys(19-Carboxynonadecanoyl)-OH

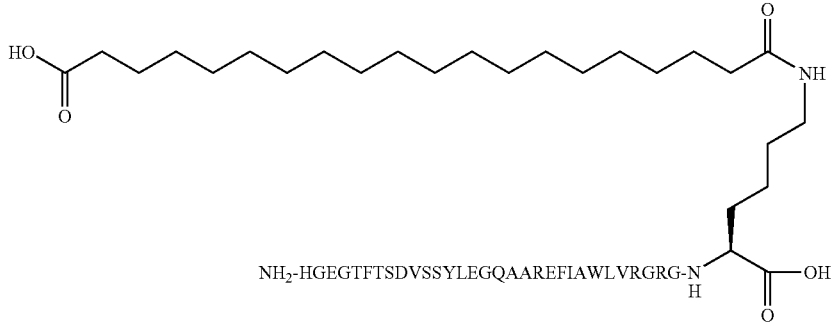

In another aspect the present invention relates to a method for increasing the time of action in a patient of a GLP-1 analog, characterised in acylating said GLP-1 analog with a diacid directly on the C-terminal amino acid residue of said GLP-1 analog.

In another aspect the present invention relates to a method for increasing the time of action in a patient of a GLP-1 analog to more than about 40 hours, characterised in modifying at least one of the amino acid residues in positions 7 and 8 of a GLP-1 (7-37) peptide or an analog thereof, and directly acylating the C-terminal amino acid residue of the GLP-1 analog with a diacid.

The GLP-1 analogs can be produced by classical peptide synthesis, e.g. solid phase peptide synthesis using t-Boc or F-Moc chemistry or other well established techniques, see the examples and e.g. Houben-Weyl, Methods of organic Chemistry, Volume E 22a, E 22b and E 22 c; Green and Wuts, "Protecting Groups in Organic Synthesis", Jogn Wiley & Sons, 1999.

The therapeutic polypeptide can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the therapeutic polypeptide may suitably be of genomic or cDNA origin, for instance obtained by preparing a genomic or cDNA library and screening for DNA sequences coding for all or part of the polypeptide by hybridisation using synthetic oligonucleotide probes in accordance with standard techniques (see, for example, Sambrook, J, Fritsch, E F and Maniatis, T, *Molecular Cloning: A Laboratory Manual*, Cold Spring Harbor Laboratory Press, New York, 1989). The DNA sequence encoding the polypeptide may also be prepared synthetically by established standard methods, e.g. the phosphoramidite method described by Beaucage and Caruthers, *Tetrahedron Letters* 22 (1981), 1859-1869, or the method described by Matthes et al., *EMBO Journal* 3 (1984), 801-805. The DNA sequence may also be prepared by polymerase chain reaction using specific primers, for instance as described in U.S. Pat. No. 4,683,202 or Saiki et al., *Science* 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well known in the art, cf. for instance Sambrook et al., supra.

The DNA sequence encoding the peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a parent peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the present peptide, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are, without limitation, *E. coli, Saccharomyces cerevisiae*, or mammalian BHK or CHO cell lines.

Examples of compounds which can be useful as GLP-1 moieties according to the present invention are described in International Patent Application No. WO 87/06941 (The General Hospital Corporation) which relates to a peptide fragment which comprises GLP-1 (7-37) and functional derivatives thereof and to its use as an insulinotropic agent.

Further GLP-1 analogues are described in International Patent Application No. 90/11296 (The General Hospital Corporation) which relates to peptide fragments which comprise GLP-1 (7-36) and functional derivatives thereof and have an insulinotropic activity which exceeds the insulinotropic activity of GLP-1 (1-36) or GLP-1 (1-37) and to their use as insulinotropic agents.

International Patent Application No. 91/11457 (Buckley et al.) discloses analogues of the active GLP-1 peptides 7-34, 7-35, 7-36, and 7-37 which can also be useful as GLP-1 moieties according to the present invention.

Pharmaceutical Compositions

Pharmaceutical compositions containing a compound according to the present invention may be prepared by conventional techniques, e.g. as described in Remington's *Pharmaceutical Sciences*, 1985 or in Remington: *The Science and Practice of Pharmacy*, 19$^{th}$ edition, 1995.

One object of the present invention is to provide a pharmaceutical formulation comprising a compound according to the present invention which is present in a concentration from about 0.1 mg/ml to about 25 mg/ml, and wherein said formulation has a pH from 2.0 to 10.0. The pharmaceutical formulation may comprise a compound according to the present invention which is present in a concentration from about 0.1 mg/ml to about 50 mg/ml, and wherein said formulation has a pH from 2.0 to 10.0. The formulation may further comprise a buffer system, preservative(s), isotonicity agent(s), chelating agent(s), stabilizers and surfactants. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds solvents and/or diluents prior to use.

In another embodiment the pharmaceutical formulation is a dried formulation (e.g. freeze-dried or spray-dried) ready for use without any prior dissolution.

In a further aspect the invention relates to a pharmaceutical formulation comprising an aqueous solution of a compound according to the present invention, and a buffer, wherein said compound is present in a concentration from 0.1 mg/ml or above, and wherein said formulation has a pH from about 2.0 to about 10.0.

In a further aspect the invention relates to a pharmaceutical formulation comprising an aqueous solution of a compound according to the present invention, and a buffer, wherein said compound is present in a concentration from 0.1 mg/ml or above, and wherein said formulation has a pH from about 7.0 to about 8.5.

In a another embodiment of the invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0. Preferably, the pH of the formulation is at least 1 pH unit from the isoelectric point of the compound according to the present invention, even more preferable the pH of the formulation is at least 2 pH unit from the isoelectric point of the compound according to the present invention.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethane, hepes, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, ethanol, chlorobutanol, and thimerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 30 mg/ml. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19$^{th}$ edition, 1995.

In a further embodiment of the invention the formulation further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a stabiliser. The use of a stabilizer in pharmaceutical compositions is well-known to the skilled person. For convenience reference is made to Remington: *The Science and Practice of Pharmacy*, 19$^{th}$ edition, 1995.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in *Spray-Drying Handbook* (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids used for preparing the compositions of the invention are those carrying a charged side chain, such as arginine, lysine, aspartic acid, and glutamic acid. In one embodiment, the amino acid used for preparing the compositions of the invention is glycine. Any stereoisomer (i.e. L or D) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D or a mixture thereof) can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention the formulation further comprises a stabiliser selected from the group of high molecular weight polymers or low molecular compounds. In a further embodiment of the invention the stabilizer is selected from polyethylene glycol (e.g. PEG 3350), polyvinylalcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention the formulation further comprises a surfactant. In a further embodiment of the invention the surfactant is selected from a detergent, ethoxylated castor oil, polyglycolized glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, starshaped PEO, polyoxyethylene and polyethylene derivatives such as alkylated and alkoxylated derivatives (tweens, e.g. Tween-20, Tween-40, Tween-80 and Brij-35), polyoxyethylene hydroxystearate, monoglycerides or ethoxylated derivatives thereof, diglycerides or polyoxyethylene derivatives thereof, alcohols, glycerol, lecitins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidyl-threonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium tauro-dihydrofusidate etc.), long-chain fatty acids and salts thereof C6-C12 (eg. oleic acid and caprylic acid), acylcarnitines and derivatives, $N^{\alpha}$-acylated derivatives of lysine, arginine or histidine, or side-chain acylated derivatives of lysine or arginine, $N^{\alpha}$-acylated derivatives of dipeptides comprising any combination of lysine, arginine or histidine and a neutral or acidic amino acid, $N^{\alpha}$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethyl-ammonio-1-propanesulfonates, 3-cholamido-1-propyldimethylammonio-1-propanesulfonate, cationic surfactants (quarternary ammonium bases) (e.g. cetyl-trimethylammonium bromide, cetylpyridinium chloride), nonionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 19$^{th}$ edition, 1995.

A composition for parenteral administration of GLP-1 compounds may, for example, be prepared as described in WO 03/002136.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a compound according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the compound, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of the compound, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenization, encapsulation, spray drying, microencapsulation, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the compound according to the present invention in the form of a nasal or pulmonal spray. As a still further option, the pharmaceutical compositions containing the compound of the invention can also be adapted to transdermal administration, e.g. by needle-free injection or from a patch, optionally an iontophoretic patch, or transmucosal, e.g. buccal, administration.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention the pharmaceutical formulation comprising the compound according to the present invention is stable for more than 6 weeks of usage and for more than 3 years of storage.

In another embodiment of the invention the pharmaceutical formulation comprising the compound according to the present invention is stable for more than 4 weeks of usage and for more than 3 years of storage.

In a further embodiment of the invention the pharmaceutical formulation comprising the compound according to the present invention is stable for more than 4 weeks of usage and for more than two years of storage.

In an even further embodiment of the invention the pharmaceutical formulation comprising the compound is stable for more than 2 weeks of usage and for more than two years of storage.

Pharmaceutical compositions containing a GLP-1 derivative according to the present invention may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of the GLP-1 derivative in the form of a nasal or pulmonal spray. As a still further option, the GLP-1 derivatives of the invention can also be administered transdermally, e.g. from a patch, optionally a iontophoretic patch, or transmucosally, e.g. bucally.

Thus, the injectable compositions of the GLP-1 derivative of the invention can be prepared using the conventional techniques of the pharmaceutical industry which involves dissolving and mixing the ingredients as appropriate to give the desired end product.

According to one procedure, the GLP-1 derivative is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

Further to the above-mentioned components, solutions containing a GLP-1 derivative according to the present invention may also contain a surfactant in order to improve the solubility and/or the stability of the GLP-1 derivative.

A composition for nasal administration of certain peptides may, for example, be prepared as described in European Patent No. 272097 (to Novo Nordisk A/S) or in WO 93/18785.

According to one preferred embodiment of the present invention, the GLP-1 derivative is provided in the form of a composition suitable for administration by injection. Such a composition can either be an injectable solution ready for use or it can be an amount of a solid composition, e.g. a lyophilised product, which has to be dissolved in a solvent before it can be injected. The injectable solution preferably contains not less than about 2 mg/ml, preferably not less than about 5 mg/ml, more preferred not less than about 10 mg/ml of the GLP-1 derivative and, preferably, not more than about 100 mg/ml of the GLP-1 derivative.

The GLP-1 derivatives of this invention can be used in the treatment of various diseases. The particular GLP-1 derivative to be used and the optimal dose level for any patient will depend on the disease to be treated and on a variety of factors including the efficacy of the specific peptide derivative employed, the age, body weight, physical activity, and diet of the patient, on a possible combination with other drugs, and on the severity of the case. It is recommended that the dosage of the GLP-1 derivative of this invention be determined for each individual patient by those skilled in the art.

In particular, it is envisaged that the GLP-1 derivative will be useful for the preparation of a medicament with a protracted profile of action for the treatment of non-insulin dependent diabetes mellitus and/or for the treatment of obesity.

In another aspect the present invention relates to the use of a compound according to the invention for the preparation of a medicament.

In one embodiment the present invention relates to the use of a compound according to the invention for the preparation of a medicament for the treatment of hyperglycemia, type 2 diabetes, impaired glucose tolerance, type 1 diabetes, obesity, hypertension, syndrome X, dyslipidemia, β-cell apoptosis, β-cell deficiency, myocardial infarction, inflammatory bowel syndrome, dyspepsia, cognitive disorders, e.g. cognitive enhancing, neuroprotection, atherosclerosis, coronary heart disease and other cardiovascular disorders.

In another embodiment the present invention relates to the use of a compound according to the invention for the preparation of a medicament for the treatment of small bowel syndrome, inflammatory bowel syndrome or Crohns disease.

In another embodiment the present invention relates to the use of a compound according to the invention for the preparation of a medicament for the treatment of hyperglycemia, type 1 diabetes, type 2 diabetes or β-cell deficiency.

The treatment with a compound according to the present invention may also be combined with combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. In the present context the expression "antidiabetic agent" includes compounds for the treatment and/or prophylaxis of insulin resistance and diseases wherein insulin resistance is the pathophysiological mechanism.

Examples of these pharmacologically active substances are: Insulin, GLP-1 agonists, sulphonylureas (e.g. tolbutamide, glibenclamide, glipizide and gliclazide), biguanides e.g. metformin, meglitinides, glucosidase inhibitors (e.g. acorbose), glucagon antagonists, DPP-IV (dipeptidyl peptidase-IV) inhibitors, gastrin, inhibitors of hepatic enzymes involved in stimulation of gluconeogenesis and/or glycogenolysis, glucose uptake modulators, thiazolidinediones such as troglitazone and ciglitazone, compounds modifying the lipid metabolism such as antihyperlipidemic agents as HMG CoA inhibitors (statins), compounds lowering food intake, RXR agonists and agents acting on the ATP-dependent potassium channel of the β-cells, e.g. glibenclamide, glipizide, gliclazide and repaglinide; Cholestyramine, colestipol, clofibrate, gemfibrozil, lovastatin, pravastatin, simvastatin, probucol, dextrothyroxine, nateglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazocin, urapidil, prazosin and terazosin; CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, gastrin and gastrin analogs.

It should be understood that any suitable combination of the compounds according to the invention with one or more of the above-mentioned compounds and optionally one or more further pharmacologically active substances are considered to be within the scope of the present invention.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

Abbreviations Used:
  r.t Room temperature
  DIEA diisopropylethylamine
  $H_2O$ water
  $CH_3CN$ acetonitrile
  DMF NN dimethylformamide
  HBTU 2-(1H-Benzotriazol-1-yl-)-1,1,3,3 tetramethyluronium hexafluorophosphate
  Fmoc 9 H-fluoren-9-ylmethoxycarbonyl
  Boc tert butyloxycarbonyl
  OtBu tert butyl ester
  tBu tert butyl
  Trt triphenylmethyl
  Pmc 2,2,5,7,8-Pentamethyl-chroman-6-sulfonyl
  Dde 1-(4,4-Dimethyl-2,6-dioxocyclohexylidene)ethyl
  DCM dichloromethane
  TIS triisopropylsilane)
  TFA: trifluoroacetic acid
  $Et_2O$: diethylether
  NMP 1-Methyl-pyrrolidin-2-one The peptide was synthesized on Fmoc protected Rink amide resin (Novabiochem) or chlorotrityl resin using Fmoc strategy on an Applied Biosystems 433A peptide synthesizer in 0.25 mmol scale using the manufacturer supplied FastMoc UV protocols which employ HBTU (2-(1H-Benzotriazol-1-yl-)-1,1,3,3 tetramethyluronium hexafluorophosphate) mediated couplings in N-methylpyrrolidone (N-methylpyrrolidone) and UV monitoring of the deprotection of the Fmoc protection group. The protected amino acid derivatives used were standard Fmoc-amino acids (Anaspec) supplied in pre-weighed cartridges suitable for the ABI433A synthesizer with the exception of unnatural aminoacids such as Fmoc-Aib-OH (Fmoc-aminoisobutyric acid).

The attachment of sidechains and linkers to specific lysine residues on the crude resin bound protected peptide was carried out in a specific position by incorporation of Fmoc-Lys (Dde)-OH during automated synthesis followed by selective deprotection with hydrazine.

Procedure for removal of Dde-protection. The resin (0.25 mmol) was placed in a manual shaker/filtration apparatus and treated with 2% hydrazine in N-methylpyrrolidone (20 ml, 2×12 min) to remove the DDE group and wash with N-methylpyrrolidone (4×20 ml).

Procedure for Attachment of Sidechains to Lysine Residues.

The amino acid (4 molar equivalents relative to resin) was dissolved in N-methyl pyrrolidone/methylene chloride (1:1, 10 ml). Hydroxybenzotriazole (HOBt) (4 molar equivalents relative to resin) and diisopropylcarbodiimide (4 molar equivalents relative to resin) was added and the solution was stirred for 15 min. The solution was added to the resin and diisopropyethylamine (4 molar equivalents relative to resin) was added. The resin was shaken 24 hours at room temperature. The resin was washed with N-methylpyrrolidone (2×20 ml), N-methylpyrrolidone/Methylene chloride (1:1) (2×20 ml) and methylene chloride (2×20 ml).

Procedure for removal of Fmoc-protection: The resin (0.25 mmol) was placed in a filter flask in a manual shaking apparatus and treated with N-methylpyrrolidone/methylene chloride (1:1) (2×20 ml) and with N-methylpyrrolidone (1×20 ml), a solution of 20% piperidine in N-methylpyrrolidone (3×20 ml, 10 min each). The resin was washed with N-methyl pyrrolidone (2×20 ml), N-methylpyrrolidone/Methylene chloride (1:1) (2×20 ml) and methylene chloride (2×20 ml).

Procedure for Cleaving the Peptide Off the Resin:

The peptide was cleaved from the resin by stirring for 180 min at room temperature with a mixture of trifluoroacetic acid, water and triisopropylsilane (95:2.5:2.5). The cleavage mixture was filtered and the filtrate was concentrated to an oil by a stream of nitrogen. The crude peptide was precipitated from this oil with 45 ml diethyl ether and washed 3 times with 45 ml diethyl ether.

Purification: The crude peptide was purified by semi-preparative HPLC on a 20 mm×250 mm column packed with 7μ C-18 silica. Depending on the peptide two one or two purification systems were used.

TFA: After drying the crude peptide was dissolved in 5 ml 50% acetic acid $H_2O$ and diluted to 20 ml with $H_2O$ and injected on the column which then was eluted with a gradient of 40-60% CH₃CN in 0.1% TFA 10 ml/min during 50 min at 40° C. The peptide containing fractions were collected. The purified peptide was lyophilized after dilution of the eluate with water.

Ammonium sulphate: The column was equilibrated with 40% CH₃CN in 0.05M (NH₄)₂SO₄, which was adjusted to pH 2.5 with concentrated H₂SO₄. After drying the crude peptide was dissolved in 5 ml 50% acetic acid H₂O and diluted to 20 ml with H₂O and injected on the column which then was eluted with a gradient of 40%-60% CH₃CN in 0.05M (NH₄)₂SO₄, pH 2.5 at 10 ml/min during 50 min at 40° C. The peptide containing fractions were collected and diluted with 3 volumes of H₂O and passed through a Sep-Pak® C18 cartridge (Waters part. #:51910) which has been equilibrated with 0.1% TFA. It was then eluted with 70% CH₃CN containing 0.1% TFA and the purified peptide was isolated by lyophilisation after dilution of the eluate with water.

The final product obtained was characterised by analytical RP-HPLC (retention time) and by LCMS The RP-HPLC analysis was performed using UV detection at 214 nm and a Vydac 218TP54 4.6 mm×250 mm 5µ C-18 silica column (The Separations Group, Hesperia, USA) which was eluted at 1 ml/min at 42° C. Two different elution conditions were used:

A1: Equilibration of the column with in a buffer consisting of 0.1 M (NH₄)₂SO₄, which was adjusted to pH 2.5 with concentrated H₂SO₄ and elution by a gradient of 0% to 60% CH₃CN in the same buffer during 50 min.

B1: Equilibration of the column with 0.1% TFA/H₂O and elution by a gradient of 0% CH₃CN/0.1% TFA/H₂O to 60% CH₃CN/0.1% TFA/H₂O during 50 min.

B6: Equilibration of the column with 0.1% TFA/H₂O and elution by a gradient of 0% CH₃CN/0.1% TFA/H₂O to 90% CH₃CN/0.1% TFA/H₂O during 50 min.

LCMS was performed on a setup consisting of Hewlett Packard series 1100 G1312A Bin Pump, Hewlett Packard series 1100 Column compartment, Hewlett Packard series 1100 G1315A DAD diode array detector, Hewlett Packard series 1100 MSD and Sedere 75 Evaporative Light Scattering detectorcontrolled by HP Chemstation software. The HPLC pump is connected to two eluent reservoirs containing:

A: 10 mM NH₄OH in water
B: 10 mM NH₄OH in 90% acetonitrile

The analysis was performed at 23° C. by injecting an appropriate volume of the sample (preferably 20 µl) onto the column which is eluted with a gradient of A and B.

The HPLC conditions, detector settings and mass spectrometer settings used are giving in the following table.
Column Waters Xterra MS C-18×3 mm id 5 µm
Gradient 5%-100% acetonitrile linear during 6.5 min at 1.5 ml/min
Detection 210 nm (analogue output from DAD)
ELS (analogue output from ELS)
MS ionisation mode API-ES. Scan 100-1000 amu step 0.1 amu Example 1

[Aib8,Arg26,34]GLP-1 (7-37)Lys{17-carboxyheptadecanoyl}-OH

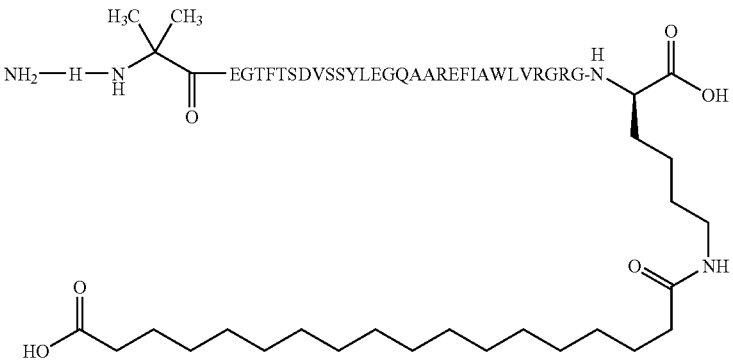

A resin (Rink amide, 0.68 mmol/g Novabiochem 0.25 mmole) was used to produce the primary sequence on an ABI433A machine according to manufacturers guidelines. All protecting groups were acid labile with the exception of the residue used in position 37 (FmocLys(ivDde)-OH, Novabiochem) allowing specific deprotection of this lysine rather than any other lysine.

Procedure

The resin (0.25 mmole) was placed in a manual shaker/filtration apparatus and treated with 2% hydrazine in N-methylpyrrolidone in (2×12 min. 2×20 ml) to remove the Dde group. The resin was washed with N-methylpyrrolidone (4×20 ml). Fmoc-8-amino-3,6-dioxaoctanoic acid (Neosystem FA03202) (4 molar equivalents relative to resin) was dissolved in N-methyl pyrrolidone/methylene chloride (1:1, 20 ml). Hydroxybenzotriazole (HOBt) (4 molar equivalents relative to resin) and diisopropylcarbodiimide (4 molar equivalents relative to resin) was added and the solution was stirred for 15 min. The solution was added to the resin and diisopropylethylamine (4 molar equivalents relative to resin) was added. The resin was shaken 24 hours at room temperature. The resin was washed with N-methylpyrrolidone (4×20 ml). A solution of 20% piperidine in N-methylpyrrolidone (3×20 ml, 10 min each) was added to the resin while shaking. The resin was washed with N-methylpyrrolidone (4×20 ml). Dodecanoic acid (4 molar equivalents relative to resin) was dissolved in N-methyl pyrrolidone/methylene chloride (1:1, 20 ml). Hydroxybenzotriazole hydrate (HOBt; H₂O) (4 molar equivalents relative to resin) and diisopropylcarbodiimide (4 molar equivalents relative to resin) were added and the solution was stirred for 15 min. The solution was added to the resin and diisopropylethylamine (4 molar equivalents relative to resin) was added. The resin was shaken 24 hours at room temperature. The resin was washed with N-methylpyrrolidone (2×20 ml), N-methylpyrrolidone/methylene chloride (1:1) (2×20 ml) and methylene chloride (2×20 ml). The peptide was cleaved from the resin by stirring for 180 min at room temperature with a mixture of trifluoroacetic acid, water and triisopropylsilane (95:2.5:2.5 15 ml). The cleavage mixture was filtered and the filtrate was concentrated to an oil in vacuum. The crude peptide was precipitated from this oil with 45 ml diethyl ether and washed 3 times with 45 ml diethyl ether. The crude peptide was purified by preparative HPLC on a 20 mm×250 mm column packed with 7μ C-18 silica. The crude peptide was dissolved in 5 ml 50% acetic acid in water and diluted to 20 ml with $H_2O$ and injected on the column which then was eluted with a gradient of 40-60% ($CH_3CN$ in water with 0.1% TFA) 10 ml/min during 50 min at 40° C. The peptide containing fractions were collected. The purified peptide was lyophilized after dilution of the eluate with water.

HPLC (method A1): RT=43.82 min

LCMS: m/z=1284.8 $(M+3H)^{3+}$ Calculated $(M+H)^+=3850.8$

Example 2

[Gly8,Arg26,34,36]GLP-1 (7-37) Lys(17-Carboxyheptadecanoylamino)-OH

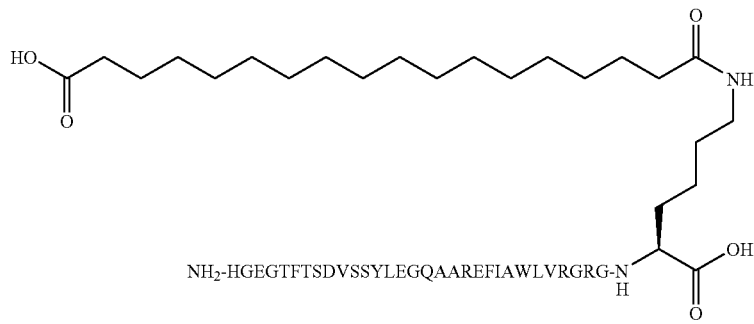

Prepared as in Example 1 and in accordance with "Synthetic methods".

HPLC (method A1): RT=43.6 min

LCMS: m/z=1275.6 $(M+3H)^{3+}$ Calculated $(M+H)^+=3822.1$

Example 3

[AlfahydroxydesaminoHis7, Gly8, Arg26,34]GLP-1 (7-37)Lys(17-carboxyheptadecanoyl)-OH

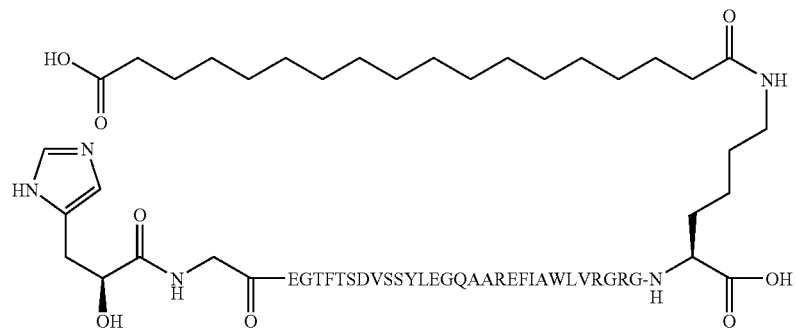

Prepared similar to Example 1 and in accordance with "Synthetic methods".
HPLC (method A1): RT=33.6 min
LCMS: m/z=1275.7 (M+3H)$^{3+}$ Calculated (M+H)$^+$=3823.3

Example 4

[Gly8, Glu22,23,30, Arg 18,26,34]GLP1 (7-37) Lys (17-carboxyheptadecanoyl)-NH$_2$

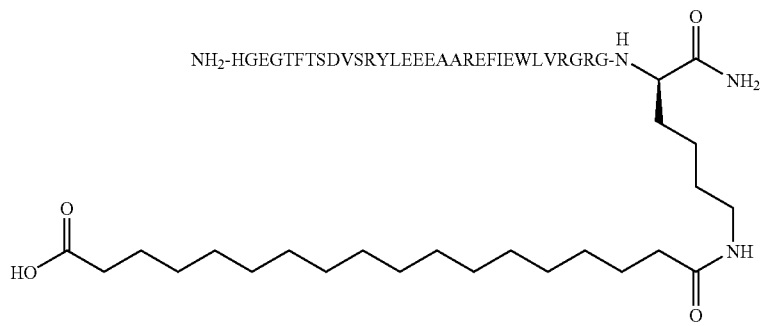

Prepared similar to Example 1 and in accordance with "Synthetic methods".
LCMS: m/z=1342.1 (M+3H)$^{3+}$ Calculated (M+H)$^+$=4021.6

Example 5

[Gly8,Arg26,34]GLP-1 (7-37)Lys(19-Carboxynonadecanoyl)-OH

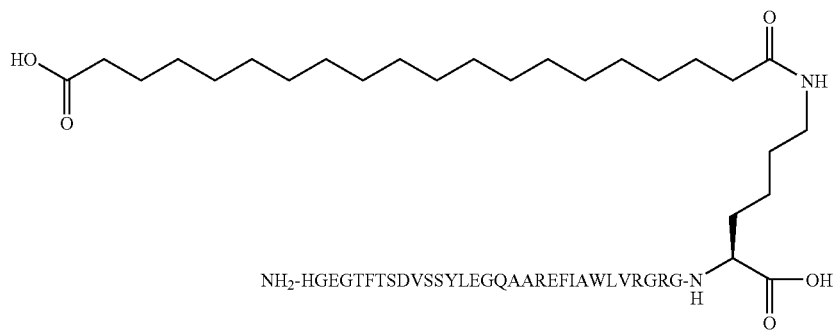

Prepared similar as Example 1 and in accordance with "Synthetic methods".
HPLC (method A1): RT=46.6 min
LCMS: m/z=1284.7 (M+3H)$^{3+}$ Calculated (M+H)$^+$=3850.4

The invention claimed is:

1. An acylated GLP-1 analog where said GLP-1 analog has a sequence according to SEQ ID NO: 1

7 8 9 10 11 12 13 14 15 16 17
His-Ala-Glu-Gly-Thr-Phe-Thr-Ser-Asp-Val-Ser-
18 19 20 21 22 23 24 25 26 27 28
Ser-Tyr-Leu-Glu-Gly-Gln-Ala-Ala-Lys-Glu-Phe-
29 30 31 32 33 34 35 36 37
Ile-Ala-Trp-Leu-Val-Lys-Gly-Arg-Gly where the Gly at position 37 is substituted by a Lys and the Ala at position 8 is substituted by Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid or (1-aminocyclooctyl) carboxylic acid and where said GLP-1 analog is acylated with a diacid attached directly to the Lys at position 37.

2. The acylated GLP-1 analog of claim 1, wherein the Lys at position 26 and the Lys at position 34 of SEQ ID NO: 1 are each substituted by an Arg.

3. The acylated GLP-1 analog of claim 2, wherein the His at position 7 has been substituted by imidazopropionyl, α-hydroxy-histidine, α-hydroxy-desamino-histidine, N-methyl-histidine, D-histidine, desamino-histidine, 2-amino-histidine, β-hydroxy-histidine, homohistidine, N$^\alpha$-acetyl-histidine, α-fluoromethyl-histidine, α-methyl-histidine, 3-pyridylalanine, 2-pyridylalanine or 4-pyridylalanine.

4. A pharmaceutical composition comprising an acylated GLP-1 analog according to claim 1 and a pharmaceutically acceptable excipient.

5. An acylated GLP-1 (7-37) analog where said GLP-1 analog has a sequence according to SEQ ID NO: 1 where the Gly at position 37 is substituted by a Lys, the His at position 7 is substituted by imidazopropionyl, α-hydroxy-histidine, α-hydroxy-desamino-histidine, N-methyl-histidine, D-histidine, desamino-histidine, 2-amino-histidine, β-hydroxy-histidine, homohistidine, N$^\alpha$-acetyl-histidine, α-fluoromethyl-histidine, α-methyl-histidine, 3-pyridylalanine, 2-pyridylalanine or 4-pyridylalanine, the Ala at position 8 is substituted by Gly, Val, Ile, Leu, Ser or Thr, and where said GLP-1 analog is acylated with a diacid attached directly to the Lys at position 37.

6. The acylated GLP-1 analog of claim 5, wherein the Lys at position 26 and the Lys at position 34 are each substituted by an Arg.

7. The acylated GLP-1 analog of claim 6, wherein the Ala at position 8 is substituted by Ser.

8. A pharmaceutical composition comprising an acylated GLP-1 analog according to claim 5 and a pharmaceutically acceptable excipient.

* * * * *

UNITED STATES PATENT AND TRADEMARK OFFICE
CERTIFICATE OF CORRECTION

PATENT NO. : 7,893,017 B2
APPLICATION NO. : 11/664788
DATED : February 22, 2011
INVENTOR(S) : Lau et al.

It is certified that error appears in the above-identified patent and that said Letters Patent is hereby corrected as shown below:

In Column 31, lines 50 and 51, delete 29 30 31 32 33 34 35 36 37

„ Ile-Ala-Trp-Leu-Val-Lys-Gly-Arg-Gly „, and insert 29 30 31 32  33 34 35 36 37

-- Ile-Ala-Trp-Leu-Val-Lys-Gly-Arg-Gly --.

In Column 32, line 46, after "GLP-1", add --(7-37)--.

In Column 32, line 48, after "An acylated GLP-1 (7-37) analog where said GLP-1", add --(7-37)--.

In Column 31, lines 46 and 47, delete 7 8 9 10 11 12 13 14 15 16 17

„ His-Ala-Glu-Gly-Thr-Phe-Thr-Ser-Asp-Val-Ser- „, and insert 7   8   9  10  11  12  13  14  15  16  17

His-Ala-Glu-Gly-Thr-Phe-Thr-Ser-Asp-Val-Ser-

--                                                    --.

In Column 31, lines 48 and 49, delete 18 19 20 21 22 23 24 25 26 27 28

„ Ser-Tyr-Leu-Glu-Gly-Gln-Ala-Ala-Lys-Glu-Phe- „, and insert 18  19  20  21  22   23  24  25  26   27   28

Ser-Tyr-Leu-Glu-Gly-Gln-Ala-Ala-Lys-Glu-Phe-

--                                                   --.

Signed and Sealed this
Eleventh Day of October, 2011

David J. Kappos
*Director of the United States Patent and Trademark Office*